(12) United States Patent
Tang

(10) Patent No.: US 6,816,565 B1
(45) Date of Patent: Nov. 9, 2004

(54) MATCHED VIEW WEIGHTING METHODS AND APPARATUS USING MULTIPLE TILTED RECONSTRUCTION PLANES

(75) Inventor: Xiangyang Tang, Waukesha, WI (US)

(73) Assignee: GE Medical Systems Global Technology Company, LLC, Waukesha, WI (US)

(*) Notice: Subject to any disclaimer, the term of this patent is extended or adjusted under 35 U.S.C. 154(b) by 0 days.

(21) Appl. No.: 10/608,061

(22) Filed: Jun. 27, 2003

(51) Int. Cl.[7] .................................................. A61B 6/03
(52) U.S. Cl. ........................ 378/15; 378/4; 378/8; 378/901
(58) Field of Search .......................... 378/4, 8, 15, 19, 378/901

(56) References Cited

U.S. PATENT DOCUMENTS

| | | | |
|---|---|---|---|
| 5,469,487 A | * 11/1995 | Hu | 378/9 |
| 5,802,134 A | 9/1998 | Larson et al. | |
| 5,881,122 A | 3/1999 | Crawford et al. | |
| 5,909,477 A | 6/1999 | Crawford et al. | |
| 6,072,851 A | * 6/2000 | Sivers | 378/15 |
| 6,118,841 A | 9/2000 | Lai | |
| 6,185,272 B1 | 2/2001 | Hiraoglu et al. | |
| 6,195,444 B1 | 2/2001 | Simanovsky et al. | |
| 6,201,849 B1 | 3/2001 | Lai | |
| 6,256,365 B1 | 7/2001 | Lai | |
| 6,256,366 B1 | 7/2001 | Lai | |
| 6,263,008 B1 | 7/2001 | Lai | |
| 6,343,108 B1 | 1/2002 | Heuscher | |
| 6,351,514 B1 | 2/2002 | Besson | |
| 6,490,333 B1 | 12/2002 | Hsieh | |
| 6,574,298 B2 | 6/2003 | Heuscher | |
| 2003/0123614 A1 | * 7/2003 | Silver et al. | 378/146 |

* cited by examiner

*Primary Examiner*—David V Bruce
(74) *Attorney, Agent, or Firm*—Carl B. Horton, Esq.; Armstrong Teasdale LLP

(57) ABSTRACT

A method for Computed Tomography scanners using multiple tilted reconstruction planes includes view weighting data in accordance with $$\chi(\beta, \gamma) = \begin{cases} w_b & 0 \leq \beta \leq 2\gamma_m - 2\gamma \\ 1 & 2\gamma_m - 2\gamma < \beta \leq \pi - 2\gamma\omega(\beta, \gamma) = \\ & 3\chi^2(\beta, \gamma) - 2\chi^3(\beta, \gamma) \text{ where } \beta \\ w_t & \pi - 2\gamma < \beta \leq \pi + 2\gamma_m \end{cases}$$

is a central view angle, $\gamma$ is a fan angle, $\gamma_m$ is a maximum half fan angle of an x-ray beam, and $w_b$ and $w_t$ are each weights no greater than 1.

27 Claims, 8 Drawing Sheets

| Object No | Object simulated | Attenuation property | Geometry (mm) (a, b, c) |
|---|---|---|---|
| 1 | Body trunk | Water | 200, 130, 100 |
| 2 | Rib | Bone | 4.5, 4.5, 92 |
| 3 | Rib | Bone | 4.5, 4.5, 92 |
| 4 | Rib | Bone | 4.5, 4.5, 4.5 |
| 5 | Rib | Bone | 4.5, 4.5, 4.5 |
| 6 | Rib | Bone | 4.5, 4.5, 4.5 |
| 7 | Spine | Bone | 12.7, 12.7, 100 |
| 8 | Air gut | Air | 19.1, 19.1, 19.1 |

FIG. 11

MATCHED VIEW WEIGHTING METHODS AND APPARATUS USING MULTIPLE TILTED RECONSTRUCTION PLANES

BACKGROUND OF THE INVENTION

This invention relates generally to computed tomography (CT) and more particularly to matched view weighting methods for computed tomography scanners using multiple tilted reconstruction planes.

A single tilted-plane-based reconstruction (sTPR) algorithm has been proposed to combat cone beam and helical artifacts in helical multi-detector-row CT. Each tilted reconstruction plane (RP) in sTPR uses two freedoms of rotation. A virtual x-ray source trajectory (VT) is defined as the intersection of a RP with the cylinder containing an actual helical x-ray source trajectory (AT) to reconstruct an image on each tilted RP. The error between VT and AT (namely trajectory error) is globally minimized and symmetric if the central intersection point between a RP and an AT is taken as the origin. However, noise characteristics of sTPR may be compromised because only short scan (180°+fan angle) projection data are used to reconstruct an image on a tilted RP. To improve the noise characteristics of sTPR, a multiple-tilted-plane-based reconstruction (mTPR) algorithm has been proposed, in which each tilted RP uses three freedoms of rotation. As a result, the trajectory error in mTPR is no longer globally minimized and symmetric.

BRIEF DESCRIPTION OF THE INVENTION

In one aspect, a method for Computed Tomography scanners using multiple tilted reconstruction planes is provided. The method includes view weighting data in accordance with $$\chi(\beta, \gamma) = \begin{cases} w_b & 0 \le \beta \le 2\gamma_m - 2\gamma \\ 1 & 2\gamma_m - 2\gamma < \beta \le \pi - 2\gamma\omega(\beta, \gamma) = \\ & 3\chi^2(\beta, \gamma) - 2\chi^3(\beta, \gamma) \text{ where } \beta \\ w_t & \pi - 2\gamma < \beta \le \pi + 2\gamma_m \end{cases}$$

is a central view angle, $\gamma$ is a fan angle, $\gamma_m$ is a maximum half fan angle of an x-ray beam, and $w_b$ and $w_t$ are each weights no greater than 1.

In another aspect, a Computed Tomography (CT) system includes an x-ray source, a detector positioned to receive x-rays emitted from the source, and a computer operationally coupled to the source and the detector. The computer is configured to receive data from a scan of an object, and weight the received data in accordance with $$\chi(\beta, \gamma) = \begin{cases} w_b & 0 \le \beta \le 2\gamma_m - 2\gamma \\ 1 & 2\gamma_m - 2\gamma < \beta \le \pi - 2\gamma\omega(\beta, \gamma) = \\ & 3\chi^2(\beta, \gamma) - 2\chi^3(\beta, \gamma) \text{ where } \beta \\ w_t & \pi - 2\gamma < \beta \le \pi + 2\gamma_m \end{cases}$$

is a central view angle, $\gamma$ is a fan angle, $\gamma_m$ is a maximum half fan angle of an x-ray beam, and $w_b$ and $w_t$ are each weights no greater than 1.

In another aspect, a method of obtaining and using weights is provided. The method includes setting $$w_b = \frac{e_t}{e_t + e_b} \text{ and } w_t = \frac{e_b}{e_t + e_b}$$

with $$e_b = \int_0^{\frac{\pi}{2}+\gamma_m} |AT(\beta) - VT(\beta)| d\beta \text{ and}$$

$$e_t = \int_{\frac{\pi}{2}+\gamma_m}^{\pi+2\gamma_m} |AT(\beta) - VT(\beta)| d\beta$$

wherein AT(β) is an actual helical x-ray source trajectory (AT) of β and VT(β) is a virtual x-ray source trajectory (VT) of β, and weighting image data with $w_b$ and $w_t$ prior to filtering and backprojecting the image data to reconstruct an image.

In still another aspect, a computer readable medium encoded with a program configured to instruct a computer is provided. The program is configured to instruct the computer to receive data from a scan of an object, and weight the received data in accordance with $$\chi(\beta, \gamma) = \begin{cases} w_b & 0 \le \beta \le 2\gamma_m - 2\gamma \\ 1 & 2\gamma_m - 2\gamma < \beta \le \pi - 2\gamma\omega(\beta, \gamma) = \\ & 3\chi^2(\beta, \gamma) - 2\chi^3(\beta, \gamma) \text{ where } \beta \\ w_t & \pi - 2\gamma < \beta \le \pi + 2\gamma_m \end{cases}$$

is a central view angle, $\gamma$ is a fan angle, $\gamma_m$ is a maximum half fan angle of an x-ray beam, and $w_b$ and $w_t$ are each weights no greater than 1.

DETAILED DESCRIPTION OF THE INVENTION

Herein described are methods and systems to compensate for the above described asymmetry in trajectory error in mTPR, utilizing a matched view weighting (MVW) (described in detail below), which is optimal from the perspective of both suppressing cone beam and helical artifacts and maintaining noise characteristics.

The apparatus and methods are illustrated with reference to the figures wherein similar numbers indicate the same elements in all figures. Such figures are intended to be illustrative rather than limiting and are included herewith to facilitate explanation of an exemplary embodiment of the apparatus and methods of the invention.

In some known CT imaging system configurations, an x-ray source projects a fan-shaped beam which is collimated to lie within an X-Y plane of a Cartesian coordinate system and generally referred to as an "imaging plane". The x-ray beam passes through an object being imaged, such as a patient. The beam, after being attenuated by the object, impinges upon an array of radiation detectors. The intensity of the attenuated radiation beam received at the detector array is dependent upon the attenuation of an x-ray beam by the object. Each detector element of the array produces a separate electrical signal that is a measurement of the beam intensity at the detector location. The intensity measurements from all the detectors are acquired separately to produce a transmission profile.

In third generation CT systems, the x-ray source and the detector array are rotated with a gantry within the imaging plane and around the object to be imaged such that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector.

In an axial scan, the projection data is processed to reconstruct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a cathode ray tube display.

To reduce the total scan time, a "helical" scan may be performed. To perform a "helical" scan, the patient is moved while the data for the prescribed number of slices is acquired. Such a system generates a single helix from a fan beam helical scan. The helix mapped out by the fan beam yields projection data from which images in each prescribed slice may be reconstructed. To further improve the performance of the CT system, multi-slice CT systems are built. In such systems, multiple projections are acquired simultaneously with multiple detector rows. For example, by extending the x-ray width in the z-axis forming a cone beam, cone beam helical scans are performed.

Reconstruction algorithms for helical scanning typically use helical weighing algorithms that weight the collected data as a function of view angle and detector channel index. Specifically, prior to a filtered backprojection process, the data is weighted according to a helical weighing factor, which is a function of both the gantry angle and detector angle. The weighted data is then processed to generate CT numbers and to construct an image that corresponds to a two dimensional slice taken through the object.

As used herein, an element or step recited in the singular and preceded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. Therefore, as used herein the term "image" broadly refers to both viewable images and data representing a viewable image. However, many embodiments generate (or are configured to generate) at least one viewable image.

Additionally, although described in a medical setting, it is contemplated that the benefits of the invention accrue to all CT systems including industrial CT systems such as, for example, but not limited to, a baggage scanning CT system typically used in a transportation center such as, for example, but not limited to, an airport or a rail station.

Figure 1:
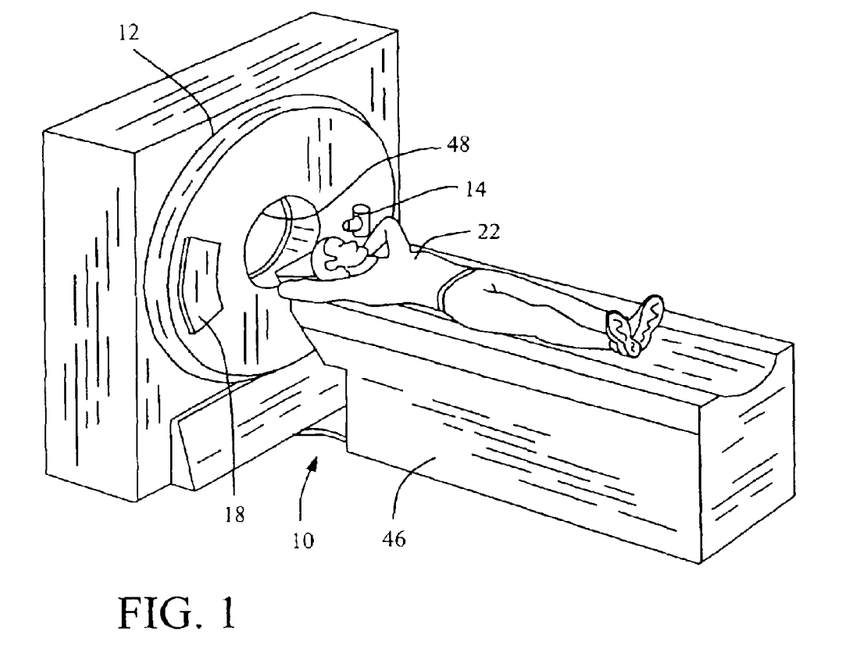
FIG. 1 is a pictorial view of a CT imaging system embodiment.
Figure 2:
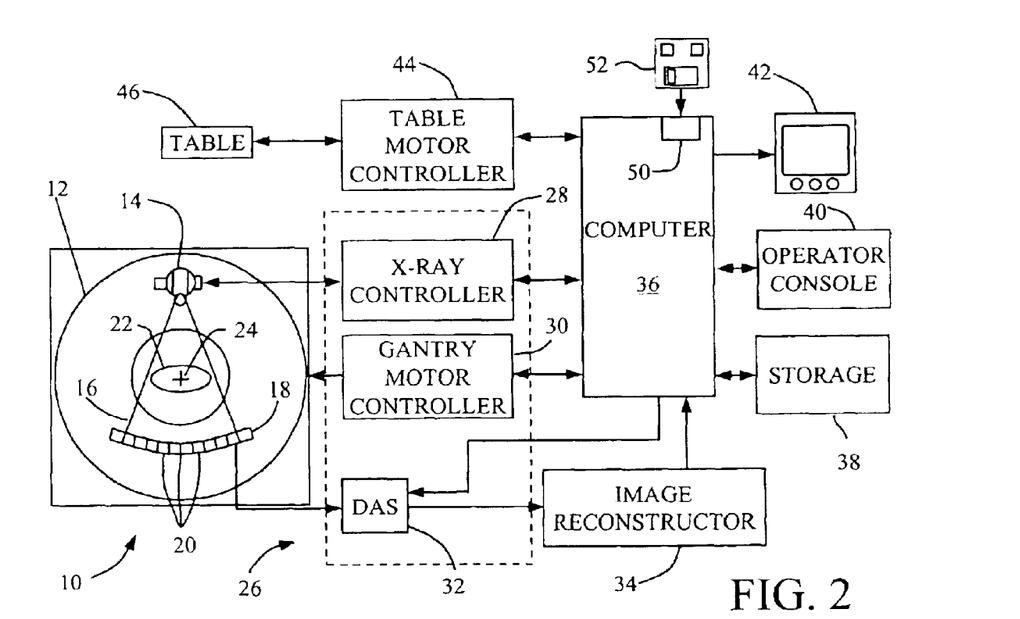
FIG. 2 is a block schematic diagram of the system illustrated in FIG. 1.

Referring to FIGS. 1 and 2, a multi-slice scanning imaging system, for example, a Computed Tomography (CT) imaging system 10, is shown as including a gantry 12 representative of a "third generation" CT imaging system. Gantry 12 has an x-ray source 14 that projects a beam of x-rays 16 toward a detector array 18 on the opposite side of gantry 12. Detector array 18 is formed by a plurality of detector rows (not shown) including a plurality of detector elements 20 which together sense the projected x-rays that pass through an object, such as a medical patient 22 between array 18 and source 14. Each detector element 20 produces an electrical signal that represents the intensity of an impinging x-ray beam and hence can be used to estimate the attenuation of the beam as it passes through object or patient 22. During a scan to acquire x-ray projection data, gantry 12 and the components mounted therein rotate about a center of rotation 24. FIG. 2 shows only a single row of detector elements 20 (i.e., a detector row). However, multi-slice detector array 18 includes a plurality of parallel detector rows of detector elements 20 such that projection data corresponding to a plurality of quasi-parallel or parallel slices can be acquired simultaneously during a scan to enable cone beam helical scans.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high-speed image reconstruction. The reconstructed image is applied as an input to a computer 36 which stores the image in a storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

In one embodiment, computer 36 includes a device 50, for example, a floppy disk drive, CD-ROM drive, DVD drive, magnetic optical disk (MOD) device, or any other digital device including a network connecting device such as an Ethernet device for reading instructions and/or data from a computer-readable medium 52, such as a floppy disk, a CD-ROM, a DVD or an other digital source such as a network or the Internet, as well as yet to be developed digital means. In another embodiment, computer 36 executes instructions stored in firmware (not shown). Computer 36 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein.

Figure 3:
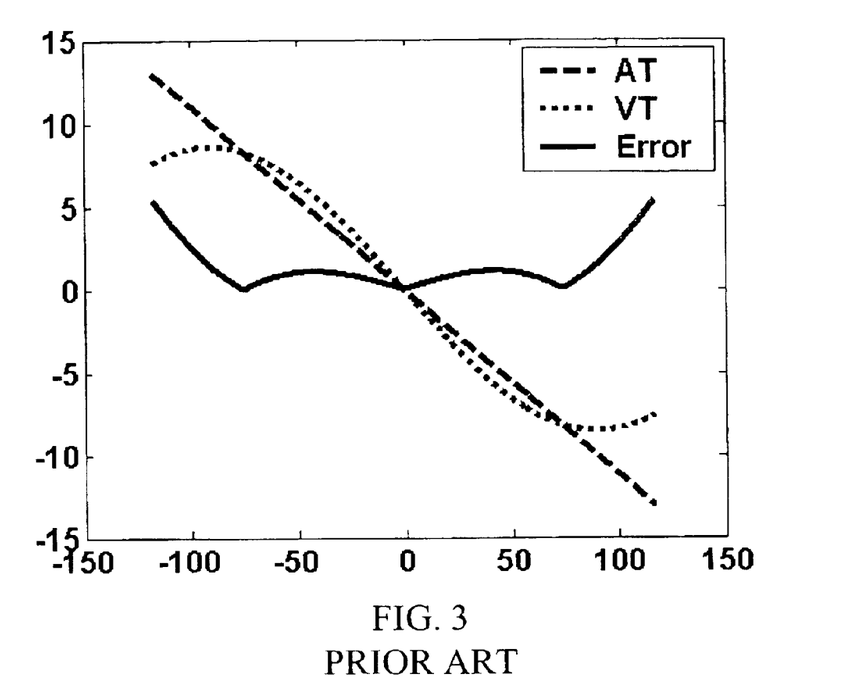
FIG. 3 illustrates that a trajectory error in sTPR is globally minimized and symmetric over view angle.
Figure 4:
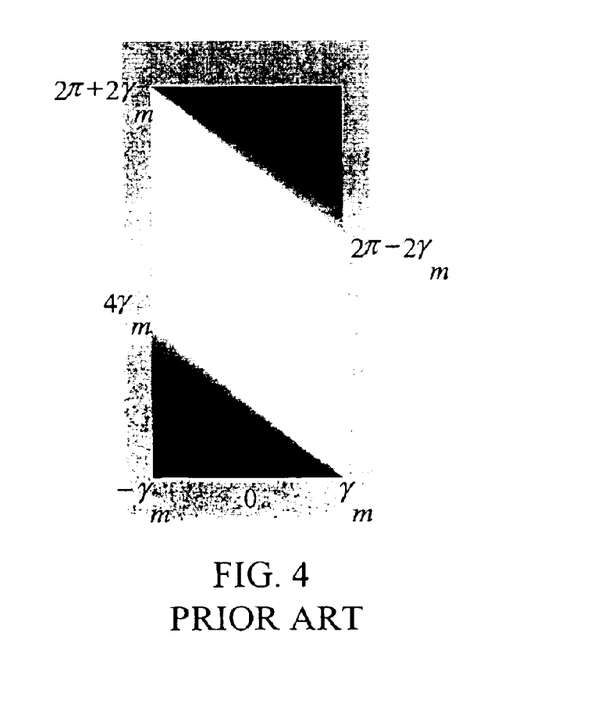
FIG. 4 illustrates a 2D intensity distribution of a view weighting function.
Figure 5:
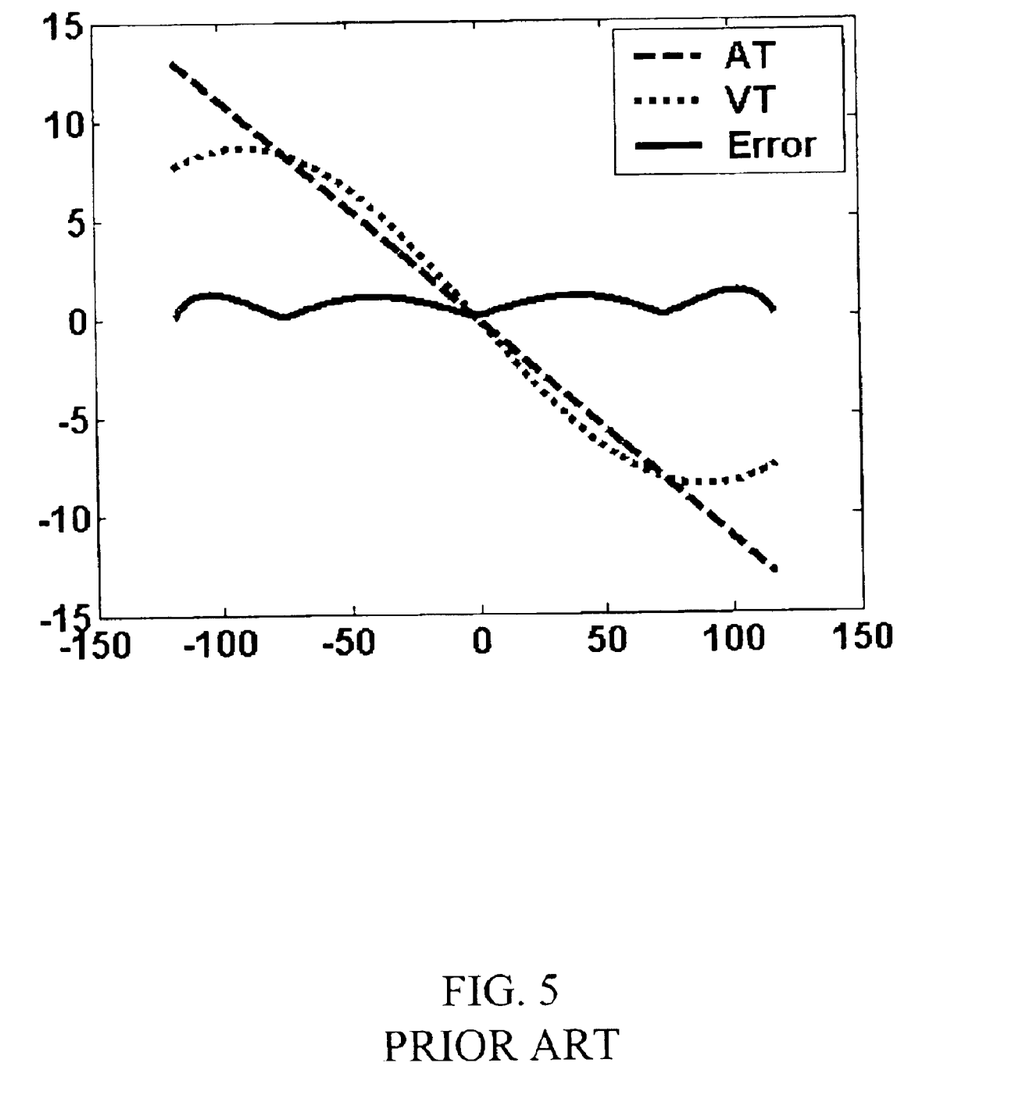
FIG. 5 illustrates a weighted trajectory error (mm) by applying the view weighting function shown in FIG. 4 on the trajectory error shown in FIG. 3.

FIG. 3 illustrates that the trajectory error in sTPR is globally minimized and symmetric over view angle. More specifically, FIG. 3 illustrates a variation of trajectory error (mm) as a function over central view angle $\beta$ (°) in sTPR (detector row number: 64, detector row width: 0.625 mm, and normalized pitch of 1.0). A few view weighting functions, most of which are symmetric about a central view angle, have been proposed to reconstruct short scan data. For instance, $$\chi(\beta, \gamma) = \begin{cases} 0.5 \frac{\beta}{\gamma_m - \gamma} & 0 \leq \beta \leq 2\gamma_m - 2\gamma \\ 1 & 2\gamma_m - 2\gamma < \beta \leq \pi - 2\gamma \\ 0.5 \frac{\pi + 2\gamma_m - \beta}{\gamma_m + \gamma} & \pi - 2\gamma < \beta \leq \pi + 2\gamma_m \end{cases} \quad (1)$$

$$\omega(\beta, \gamma) = 3\chi^2(\beta, \gamma) - 2\chi^3(\beta, \gamma) \quad (2)$$

where $\beta$ is the central view angle, $\gamma$ the fan angle, and $\gamma_m$ the maximum half fan angle of an x-ray beam (see FIG. 4 which illustrates a 2D intensity distribution of the view weighting function given in (1) and (2) for fan beam short scan data wherein white pixels correspond to 1.0, gray to 0.0~1.0 and black to 0.0). This view weighing function appears apt for sTPR because its symmetric distribution matches the trajectory error. FIG. 5 illustrates a weighted trajectory error (mm) by applying the view weighting function shown in FIG. 4 on the trajectory error shown in FIG. 3 (detector row number: 64, detector row width: 0.625 mm, normalized pitch 1.0).

Figure 6:
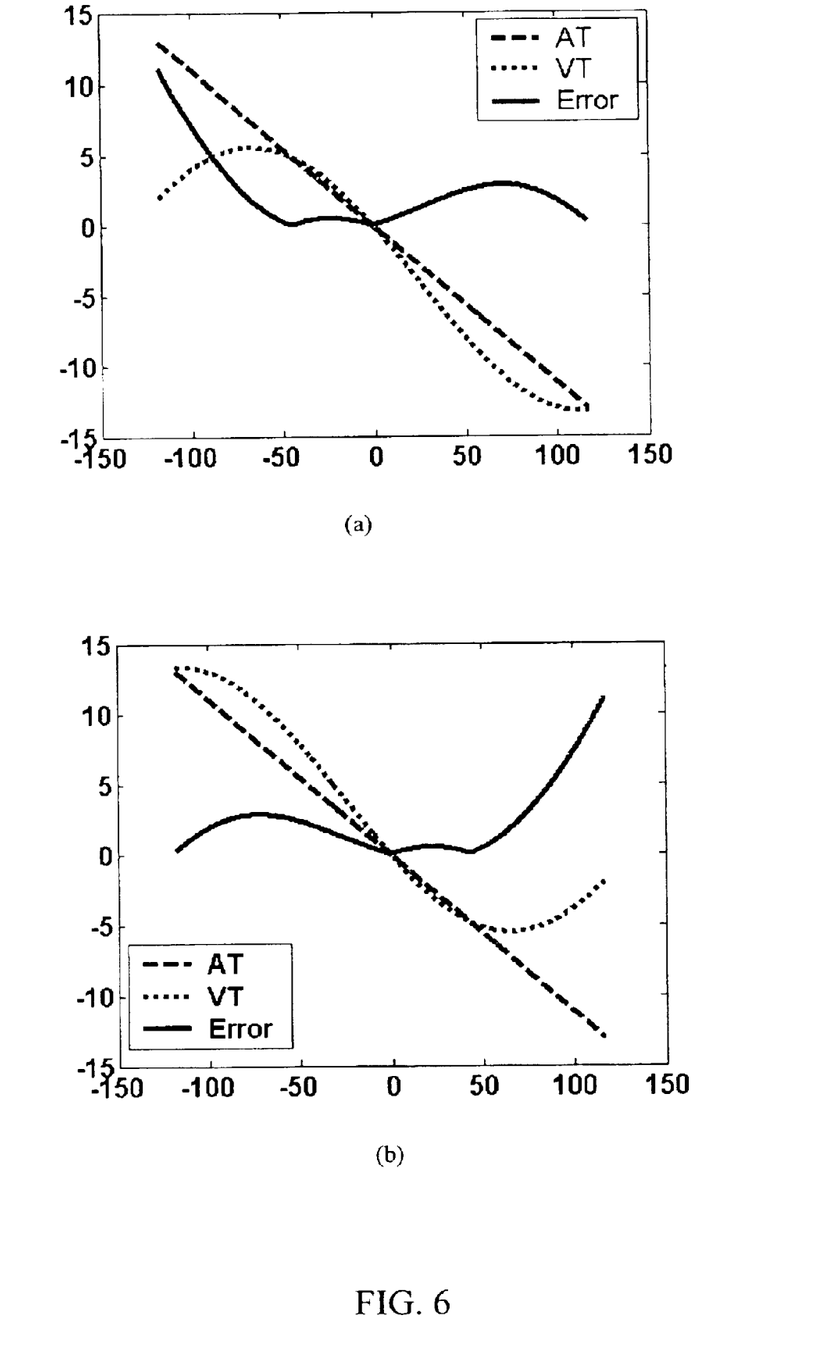
FIG. 6 illustrates a trajectory error in mTPR increases and no longer symmetric about the central attachment point.

However, and now referring to mTPR, each tilted RP in mTPR makes use of three freedoms of rotation along x, y and z axes respectively. The rotations along y and z axes are the same as that in sTPR to fit a helical source trajectory, and that along x axis is to improve noise characteristics or dose efficiency. Intuitively, due to the rotation along the x axis, each tilted RP in sTPR splits into several titled RPs in mTPR, and these RPs deviate from the optimized pose determined in sTPR. Consequently, the trajectory error in mTPR increases and is no longer symmetric about the central attachment point as shown in FIG. 6, where FIG. 6a illustrates a distribution corresponding to the RP rotating along x axis toward −z; and FIG. 6b illustrates a distribution corresponding to the RP rotating along x axis toward +z; (detector row number 64; detector row width 0.625 mm; normalized helical pitch 1.0; only double tilted reconstruction planes are considered). Eventually, the severity of cone beam and helical artifacts are determined by weighted trajectory error. A way to compensate for the asymmetry in trajectory error is to use an opposite asymmetry in view weighting function. Extreme examples of such opposite asymmetric view weighting functions are given by $$w_t(\beta, \gamma) = \begin{cases} 1 & 0 \leq \beta \leq \pi - 2\gamma \\ 0 & \pi - 2\gamma \leq \beta \leq \pi + 2\gamma_m \end{cases} \quad (3)$$

$$w_b(\beta, \gamma) = \begin{cases} 0 & 0 \leq \beta \leq 2\gamma_m - 2\gamma \\ 1 & 2\gamma_m - 2\gamma \leq \beta \leq \pi + \gamma_m \end{cases} \quad (4)$$

Figure 7:
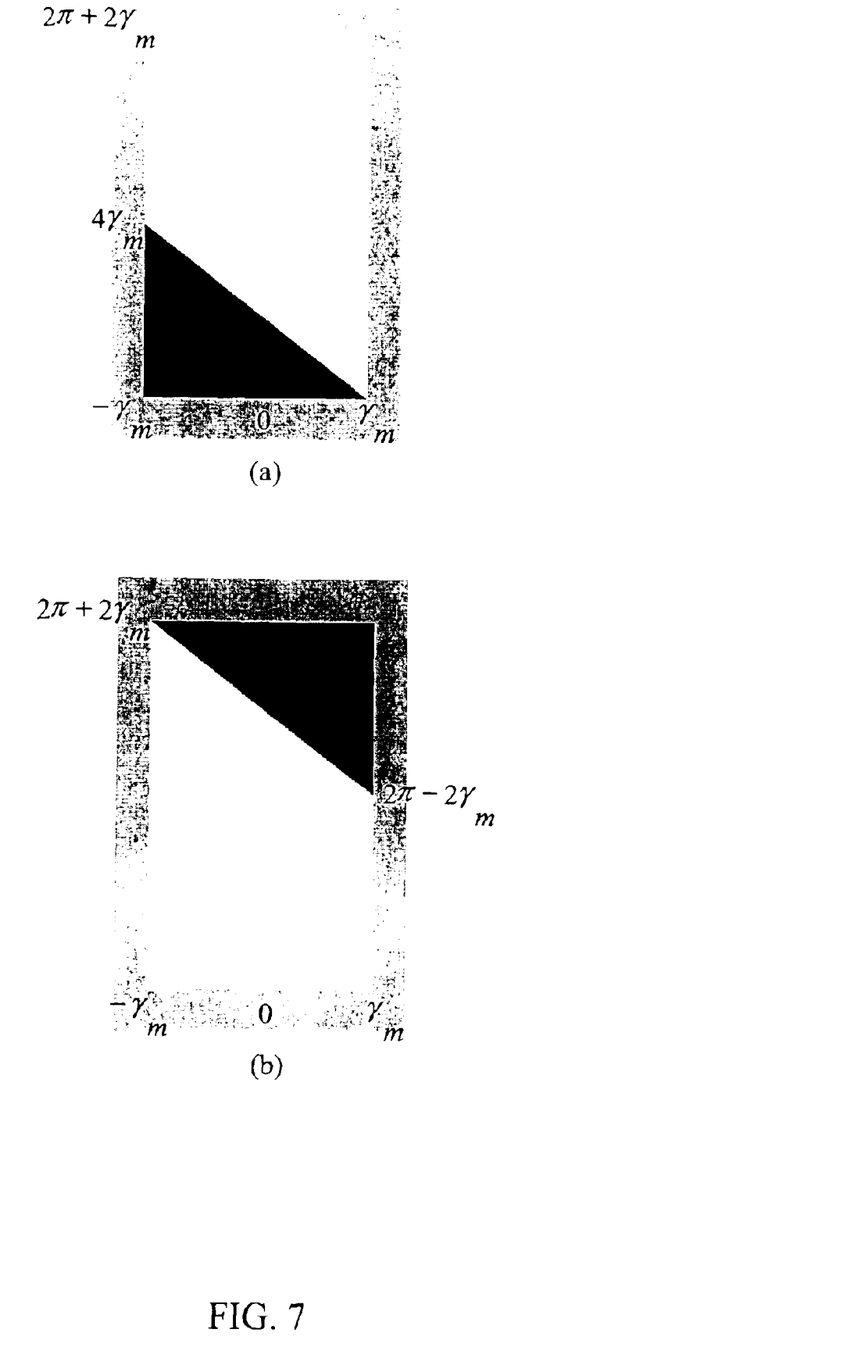
FIG. 7 graphically illustrates a view weighting function.
Figure 8:
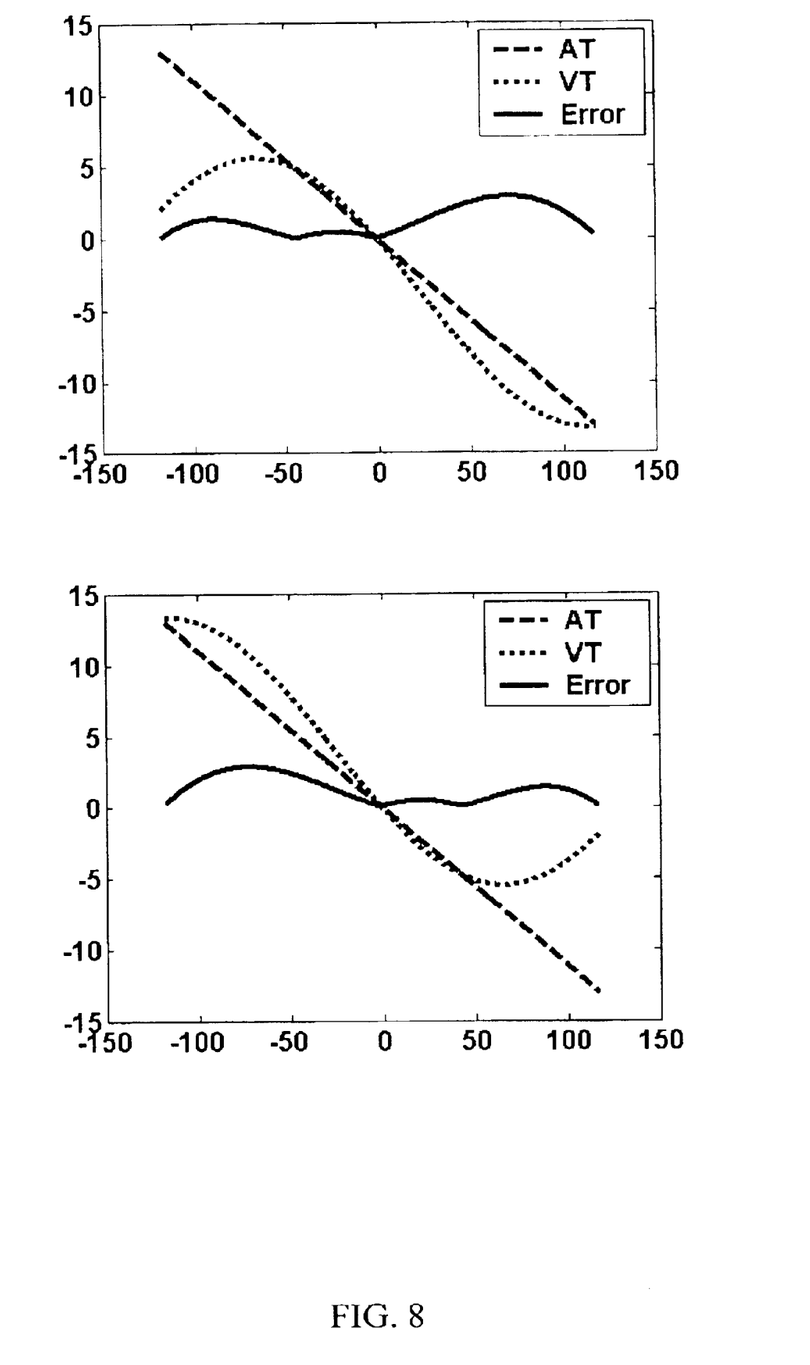
FIG. 8 illustrates a weighted trajectory error (mm) by applying the view weighting function shown in FIG. 7.

FIG. 7 graphically illustrates the view weighting function given by (3) and (4). FIG. 8 illustrates that the view weighting function given by (3) and (4) is the best in terms of weighted trajectory error in mTPR, but the worst from the perspective of noise characteristics, since all the weighting factors equal to either one or zero.

An optimized view weighting function of mTPR is $$\chi(\beta, \gamma) = \begin{cases} w_b & 0 \leq \beta \leq 2\gamma_m - 2\gamma \\ 1 & 2\gamma_m - 2\gamma < \beta \leq \pi - 2\gamma \\ w_t & \pi - 2\gamma < \beta \leq \pi + 2\gamma_m \end{cases} \quad (5)$$

$$\omega(\beta, \gamma) = 3\chi^2(\beta, \gamma) - 2\chi^3(\beta, \gamma) \quad (6)$$

which matches the asymmetric distribution of trajectory error in mTPR. The weighting factors $w_b$ and $w_t$ corresponding to the bottom and upper redundant areas respectively are adaptively determined by $$w_b = \frac{e_t}{e_t + e_b} \quad (7)$$

$$w_t = \frac{e_b}{e_t + e_b} \quad (8)$$

where $$e_b = \int_0^{\frac{\pi}{2} + \gamma_m} |AT(\beta) - VT(\beta)| d\beta \quad (9)$$

$$e_t = \int_{\frac{\pi}{2} + \gamma_m}^{\pi + 2\gamma_m} |AT(\beta) - VT(\beta)| d\beta \quad (10)$$

Figure 9:
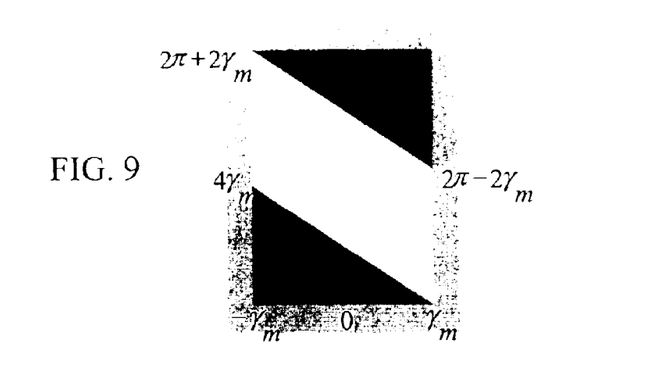
FIG. 9 graphically illustrates a view weighting function.

Obviously, there exist discontinuities in the view weighting function given in (5)–(10). To reduce or eliminate streak artifacts in reconstructed tomographic images caused by those discontinuities, feathering, such as that described by C. R. Crawford and K. F. King, "Computed tomography scanning with simultaneous patient translation," *Med. Phys.* 17(6), pp967–982, 1990., may be applied while view weighting. FIG. 9 graphically illustrates the view weighting function given in (5)–(10).

Figure 10:
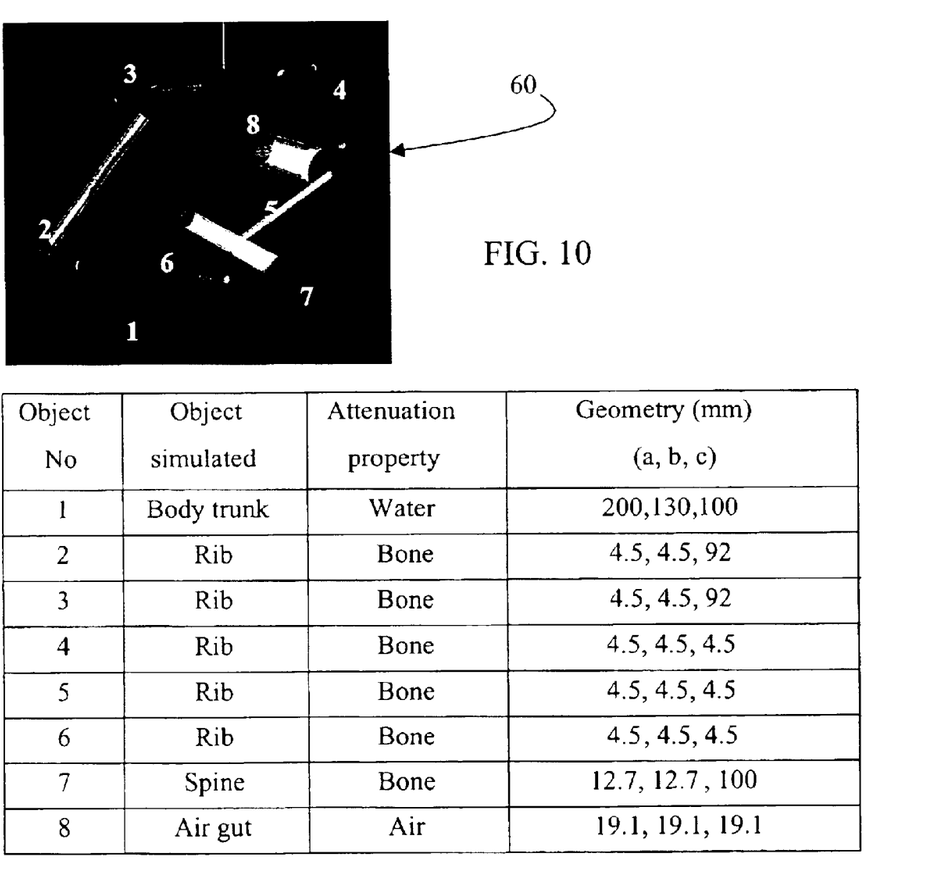
FIG. 10 is a three dimensional perspective view of a helical body phantom (HBP).

FIG. 10 is a three dimensional perspective view of a helical body phantom (HBP) 60 which was employed to evaluate the imaging performance of the herein described matched view weighting function in mTPR. HBP 60 is configured to simulate the human thorax under helical scanning. HBP 60 includes a plurality of small cylindrical rods which are oblique relative to a gantry's rotation axis to simulate the ribs in a human thorax, which would highlight helical artifacts due to projection data inconsistence in helical scanning. The x-ray technique used for scanning HBP phantom 60 was 120 kVp, 200 mA and 1.0 sec. per gantry rotation, and the scanner possessed 16 detector rows at width 1.25 mm running at normalized pitch 15/16. A quantitative evaluation of the helical artifacts and noise characteristics was conducted by measuring a global helical artifact index (ART$^+$) as discussed by T. L. Toth and P.

Simoni, ("A quantitative measure of CT helical Artifacts," Radiology, 221(P), pp218, 2001.) and the standard deviation ($SD^+$) within a square containing 20 by 20 pixels at the isocenter. For simplicity, only double tilted reconstruction planes were used at each central view position. The tomographic image on a RP was obtained through fan beam, rather than parallel beam, reconstruction algorithm. Both $w_b$ and $w_t$ were varied in step 0.1 respectively in the quantitative evaluation as seen in table 1.

TABLE 1

| $w_1$ | $w_b$ | Sd+ | Art+ |
|---|---|---|---|
| 1.000 | 0.000 | 42.214 | 14.647 |
| 0.900 | 0.100 | 41.537 | 14.182 |
| 0.800 | 0.200 | 41.205 | 13.525 |
| 0.700 | 0.300 | 40.942 | 13.006 |
| 0.600 | 0.400 | 40.776 | 12.495 |
| 0.500 | 0.500 | 40.620 | 12.278 |
| 0.400 | 0.600 | 40.661 | 11.974 |
| | | | |
| 0.300 | 0.700 | 40.652 | 11.839 |
| 0.200 | 0.800 | 41.006 | 11.948 |
| 0.100 | 0.900 | 41.104 | 12.021 |
| 0.000 | 1.000 | 41.383 | 11.860 |
| CK | | 41.161 | 12.538 |

Table 1 illustrates noise characteristics and artifact indexes measured in images reconstructed by the mTPR in which the matched view weighting function is applied, where CK represents the view weighting function given in Eqs. (1)–(2), and the superscript + means tilted RP's 3rd rotation is toward +z axis. The artifact index is measured on tilted tomographic images before z-interpolation used to obtain tomographic images orthogonal to the gantry rotation axis. It is observed that, $Art^+$ reaches its maximum at $w_b=0.0$ due to a complete mismatch between the source trajectory error distribution and the view weighting function. The $Art^+$ is inversely proportional to the increment in $w_b$ and reaches the minimum at $w_b=0.7$ ($w_t=0.3$). Notice that, as shown in the shadowed row in Table 1, $w_b=0.7$ ($w_t=0.3$) is very close to the matched view weighting factor $w_b=0.608$ ($w_t=0.392$) predicted by Eqs. (7)–(10), which is consistent with the expectation on matched view weighting. Meanwhile, the artifact index corresponding to the view weighting function given in Eqs. (1)–(2) is also listed in Table 1 as a reference (CK), which is significantly larger than its counterpart corresponding to the matched view weighting at $w_b=0.608$ ($w_t=0.392$).

The noise characteristics ($Sd^+$) of the images reconstructed by the mTPR on the tilted RP are also listed in Table. 1, where the superscript + means tilted RP's 3rd rotation is toward +z axis as before. The standard deviation is measured at the isocenter of a tilted tomographic image before z-interpolation. It is observed that $Sd^+$ reaches the minimum while $w_b=w_t=0.5$, because the weighting factor equaling to 0.5 is the best from the perspective of noise characteristics. Moreover, the $Sd^+$ is quite stable between $w_b=0.5$ ($w_t=0.5$) and $w_b=0.7$ ($w_t=0.3$), and $w_b=0.608$ ($w_t=0.392$) falls into this interval. This is again consistent with the expectation on matched view weighting. Meanwhile, the noise characteristics corresponding to the view weighting function given in Eqs. (1)–(2) is also listed in Table 1 (CK), which is significantly larger than that corresponding to the matched view weighting at $w_b=0.608$ ($w_t=0.392$).

In order to suppress helical artifact as much as possible, only the projection data corresponding to an angle range of (180°+fan angle) are used to reconstruct an image on tilted reconstruction plane in single/multiple tilted-plane-based reconstruction algorithm. The view weighting functions usually used in non-tilted-plane-based short scan reconstruction can be used in sTPR because the x-ray source trajectory error distribution is symmetric about the central attachment point. However, the tilted reconstruction planes in mTPR deviates from the globally optimized pose and the resultant x-ray source trajectory error is no longer symmetric about the central attachment point. Accordingly, as illustrated above, opposite asymmetry in view weighting function is useful to maintain mTPR's capability of suppressing helical artifacts while keeping the noise characteristics good.

Figure 11:
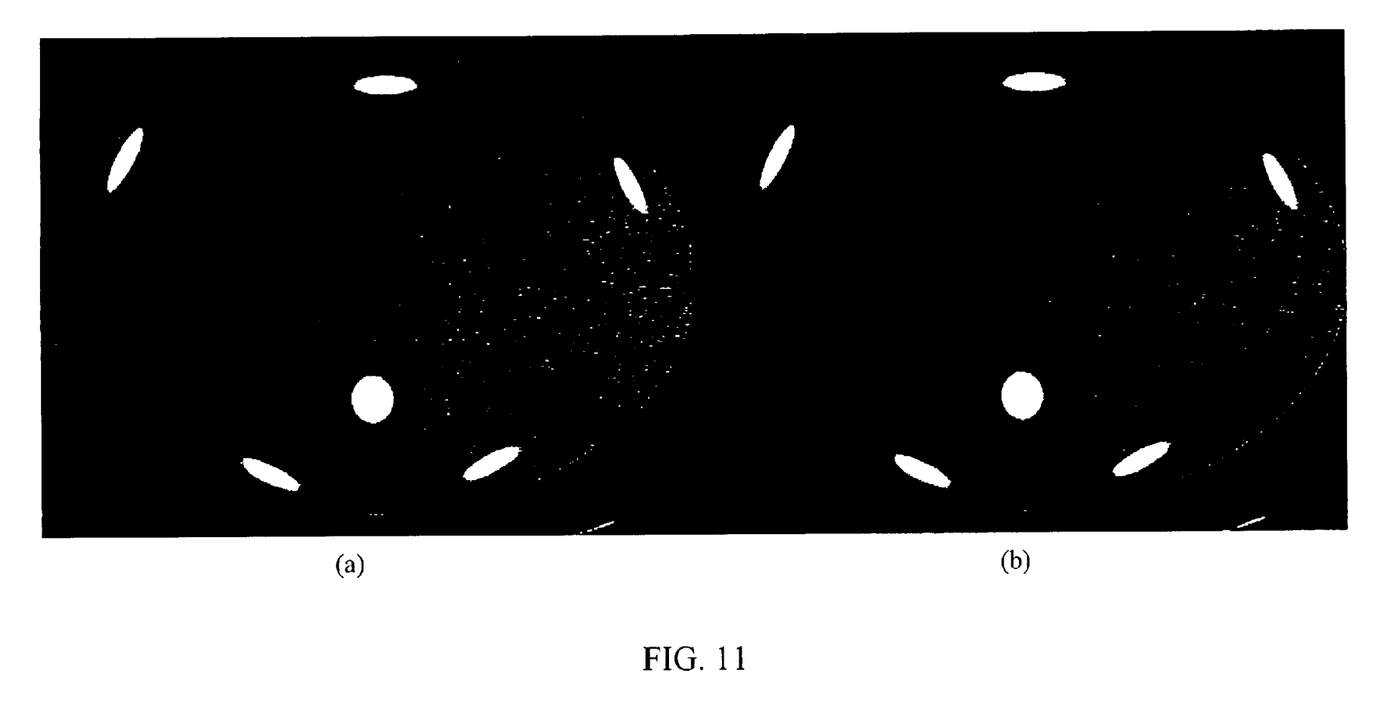
FIG. 11 illustrates two tomographic image of the HBP phantom shown in FIG. 10 reconstructed on a RP, in which the matched and non-matched view weighting functions were applied respectively before filtering and backprojection.

FIG. 11 illustrates two tomographic image of the HBP phantom reconstructed on a RP by mTPR, in which different view weighting functions were applied before filtering and backprojection. FIG. 11a illustrates the non-matched view weighting given in Eqs. (1)–(2), and FIG. 11b illustrates the matched view weighting given in Eqs. (5)–(6) at wt=0.392, wb=0.608.

It is observed that the matched view weighting function can improve both the noise characteristics and capability of suppression helical artifact significantly. Moreover, as elucidated above, the visual observation in FIG. 11 of improved noise characteristics and helical artifact suppression is reinforced by the quantitative results demonstrated in Table 1.

While the invention has been described in terms of various specific embodiments, those skilled in the art will recognize that the invention can be practiced with modification within the spirit and scope of the claims.

What is claimed is:

1. A method for Computed Tomography scanners using multiple tilted reconstruction planes, said method comprising:

view weighting data in accordance with $$\chi(\beta, \gamma) = \begin{cases} w_b & 0 \le \beta \le 2\gamma_m - 2\gamma \\ 1 & 2\gamma_m - 2\gamma < \beta \le \pi - 2\gamma \\ w_t & \pi - 2\gamma < \beta \le \pi + 2\gamma_m \end{cases}$$

$$\omega(\beta, \gamma) = 3\chi^2(\beta, \gamma) - 2\chi^3(\beta, \gamma)$$

where $\beta$ is a central view angle, $\gamma$ is a fan angle, $\gamma_m$ is a maximum half fan angle of an x-ray beam, and $w_b$ and $w_t$ are each weights no greater than 1.

2. A method in accordance with claim 1 wherein $w_b$ is calculated by $$w_b = \frac{e_t}{e_t + e_b}$$

with $$e_b = \int_0^{\frac{\pi}{2}+\gamma_m} |AT(\beta) - VT(\beta)| d\beta \text{ and}$$

$$e_t = \int_{\frac{\pi}{2}+\gamma_m}^{\pi+2\gamma_m} |AT(\beta) - VT(\beta)| d\beta$$

where $AT(\beta)$ is an actual helical x-ray source trajectory (AT) of $\beta$ and $VT(\beta)$ is a virtual x-ray source trajectory (VT) of $\beta$.

3. A method in accordance with claim 1 wherein $w_t$ is calculated by $$w_t = \frac{e_b}{e_t + e_b}$$

with $$e_b = \int_0^{\frac{\pi}{2}+\gamma_m} |AT(\beta) - VT(\beta)| d\beta \text{ and}$$

$$e_t = \int_{\frac{\pi}{2}+\gamma_m}^{\pi+2\gamma_m} |AT(\beta) - VT(\beta)| d\beta$$

where AT($\beta$) is an actual helical x-ray source trajectory (AT) of $\beta$ and VT($\beta$) is a virtual x-ray source trajectory (VT) of $\beta$.

4. A method in accordance with claim 2 wherein $w_t$ is calculated by $$w_t = \frac{e_b}{e_t + e_b}$$

with $$e_b = \int_0^{\frac{\pi}{2}+\gamma_m} |AT(\beta) - VT(\beta)| d\beta \text{ and}$$

$$e_t = \int_{\frac{\pi}{2}+\gamma_m}^{\pi+2\gamma_m} |AT(\beta) - VT(\beta)| d\beta$$

where AT($\beta$) is an actual helical x-ray source trajectory (AT) of $\beta$ and VT($\beta$) is a virtual x-ray source trajectory (VT) of $\beta$.

5. A method in accordance with claim 1 wherein $w_t$ is between 0.5 and 0.1, and $w_b$ is between 0.5 and 0.9.

6. A method in accordance with claim 1 wherein $w_b$ is between 0.5 and 0.1, and $w_t$ is between 0.5 and 0.9.

7. A method in accordance with claim 5 wherein $w_t$ is between 0.4 and 0.2, and $w_b$ is between 0.6 and 0.8.

8. A method in accordance with claim 6 wherein $w_b$ is between 0.4 and 0.2, and $w_t$ is between 0.6 and 0.8.

9. A method in accordance with claim 1 wherein $w_t$ is about 0.4 and $w_b$ is about 0.6.

10. A method in accordance with claim 1 wherein $w_t$ is about 0.6 and $w_b$ is about 0.4.

11. A Computed Tomography (CT) system comprising:
an x-ray source;
a detector positioned to receive x-rays emitted from said source; and
a computer operationally coupled to said source and said detector, said computer configured to:
receive data from a scan of an object; and
weight the received data in accordance with $$\chi(\beta, \gamma) = \begin{cases} w_b & 0 \leq \beta \leq 2\gamma_m - 2\gamma \\ 1 & 2\gamma_m - 2\gamma < \beta \leq \pi - 2\gamma \\ w_t & \pi - 2\gamma < \beta \leq \pi + 2\gamma_m \end{cases}$$

$$\omega(\beta, \gamma) = 3\chi^2(\beta, \gamma) - 2\chi^3(\beta, \gamma)$$

where $\beta$ is a central view angle, $\gamma$ is a fan angle, $\gamma_m$ is a maximum half fan angle of an x-ray beam, and $w_b$ and $w_t$ are each weights no greater than 1.

12. A system according to claim 11 wherein $w_t$ is between 0.5 and 0.1, and $w_b$ is between 0.5 and 0.9.

13. A system according to claim 11 wherein $w_t$ is between 0.5 and 0.9, and $w_b$ is between 0.5 and 0.1.

14. A system according to claim 11 wherein $w_t$ is between 0.4 and 0.2, and $w_b$ is between 0.6 and 0.8.

15. A system according to claim 11 wherein $w_t$ is between 0.6 and 0.8, and $w_b$ is between 0.4 and 0.2.

16. A system according to claim 11 wherein $w_t$ is about 0.4 and $w_b$ is about 0.6.

17. A system according to claim 11 wherein $w_t$ is about 0.6 and $w_b$ is about 0.4.

18. A method of obtaining and using weights, said method comprising:
setting $$w_b = \frac{e_t}{e_t + e_b} \text{ and } w_t = \frac{e_b}{e_t + e_b}$$

with $$e_b = \int_0^{\frac{\pi}{2}+\gamma_m} |AT(\beta) - VT(\beta)| d\beta \text{ and}$$

$$e_t = \int_{\frac{\pi}{2}+\gamma_m}^{\pi+2\gamma_m} |AT(\beta) - VT(\beta)| d\beta$$

wherein AT($\beta$) is an actual helical x-ray source trajectory (AT) of $\beta$ and VT($\beta$) is a virtual x-ray source trajectory (VT) of $\beta$; and weighting image data with $w_b$ and $w_t$ prior to filtering and backprojecting the image data to reconstruct an image.

19. A method according to claim 18 wherein $w_t$ is between 0.5 and 0.1.

20. A method according to claim 18 wherein $w_b$ is between 0.5 and 0.1.

21. A method according to claim 18 wherein $w_b$ is between 0.5 and 0.9.

22. A method according to claim 18 wherein $w_t$ is between 0.5 and 0.9.

23. A method according to claim 18 wherein $w_b$ is between 0.5 and 0.9 and $w_t$ is between 0.5 and 0.1.

24. A method according to claim 18 wherein $w_t$ is between 0.5 and 0.9 and $w_b$ is between 0.5 and 0.1.

25. A computer readable medium encoded with a program configured to instruct a computer to:
receive data from a scan of an object; and
weight the received data in accordance with $$\chi(\beta, \gamma) = \begin{cases} w_b & 0 \leq \beta \leq 2\gamma_m - 2\gamma \\ 1 & 2\gamma_m - 2\gamma < \beta \leq \pi - 2\gamma \\ w_t & \pi - 2\gamma < \beta \leq \pi + 2\gamma_m \end{cases}$$

$$\omega(\beta, \gamma) = 3\chi^2(\beta, \gamma) - 2\chi^3(\beta, \gamma)$$

where $\beta$ is a central view angle, $\gamma$ is a fan angle, $\gamma_m$ is a maximum half fan angle of an x-ray beam, and $w_b$ and $w_t$ are each weights no greater than 1.

26. A medium in accordance with claim 25 wherein said program further configured to instruct the computer to weight the received data in accordance with $$\chi(\beta, \gamma) = \begin{cases} w_b & 0 \leq \beta \leq 2\gamma_m - 2\gamma \\ 1 & 2\gamma_m - 2\gamma < \beta \leq \pi - 2\gamma \\ w_t & \pi - 2\gamma < \beta \leq \pi + 2\gamma_m \end{cases}$$

$$\omega(\beta, \gamma) = 3\chi^2(\beta, \gamma) - 2\chi^3(\beta, \gamma)$$

wherein $w_t$ is about 0.4.

27. A medium in accordance with claim 25 wherein said program further configured to weight the received data in accordance with $$\chi(\beta, \gamma) = \begin{cases} w_b & 0 \leq \beta \leq 2\gamma_m - 2\gamma \\ 1 & 2\gamma_m - 2\gamma < \beta \leq \pi - 2\gamma \\ w_t & \pi - 2\gamma < \beta \leq \pi + 2\gamma_m \end{cases}$$

$$\omega(\beta, \gamma) = 3\chi^2(\beta, \gamma) - 2\chi^3(\beta, \gamma)$$

wherein $w_b$ is about 0.6.

* * * * *